United States Patent [19]

Biziere et al.

[11] Patent Number: 4,604,383

[45] Date of Patent: Aug. 5, 1986

[54] PYRROLIDIN-2-ONES AND MEDICAMENTS CONTAINING THEM

[75] Inventors: Kathleen Biziere, Clapiers; Jean-Pierre Chambon, Montarnaud; Jean-Charles Molimard, Saint-Gely-du-Fesc, all of France

[73] Assignee: Societe Anonyme Styled: SANOFI, Paris, France

[21] Appl. No.: 628,211

[22] Filed: Jul. 5, 1984

[30] Foreign Application Priority Data

Jul. 12, 1983 [FR] France .................. 83 11636

[51] Int. Cl.$^4$ .................. C07D 207/26; C07D 409/06; A61K 31/40
[52] U.S. Cl. ........................ 514/63; 514/424; 548/110; 548/453
[58] Field of Search ............. 548/543, 110; 514/424, 514/63

[56] References Cited

U.S. PATENT DOCUMENTS 3,272,842  9/1966  Easton et al. ............... 548/543
4,198,514  4/1980  Imanishi et al. .............. 548/543

Primary Examiner—Richard L. Raymond
Assistant Examiner—D. B. Springer
Attorney, Agent, or Firm—Bacon and Thomas

[57] ABSTRACT

The invention relates to pyrrolidinones of the general formula:

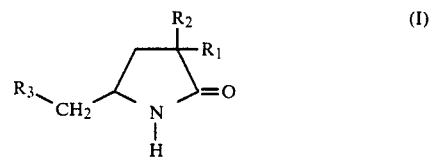

in which:

$R_1$ represents hydrogen or alkyl
$R_2$ represents alkyl, phenyl or trimethylsilyl.
$R_3$ represents 2-thienyl or a phenyl possibly substituted once or twice with halogen, methyl, methoxy or a trifluoromethyl group. It relates also to a process for the production of these compounds and to the pharmaceutical compositions containing them.

8 Claims, No Drawings

PYRROLIDIN-2-ONES AND MEDICAMENTS CONTAINING THEM

The present invention relates to pyrrolidinones of the general formula:

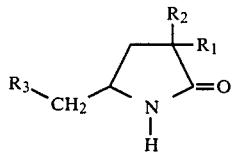

in which:
$R_1$ represents hydrogen or alkyl
$R_2$ represents alkyl, phenyl or trimethylsilyl.
$R_3$ represents 2-thienyl or phenyl optionally substituted once or twice by halogen, methyl, methoxy or a trifluoromethyl group.

Throughout the present description, the term alkyl represents a straight or branched alkyl comprising 1 to 4 carbon atoms.

These compounds have an activity on the central nervous system; they have, in particular, an anticonvulsant effect on the animal and act on the spontaneous motility.

The compounds according to the invention may be prepared by several methods of synthesis according to the value of the substituents $R_1$, $R_2$, $R_3$. The preparation is effected, either by cyclization of a gamma amino ester, or by substitutions on a pyrrolidine nucleus, these two methods being combinable.

PROCESS 1

The compounds according to the invention may be obtained by hot cyclization of a gamma amino ester:

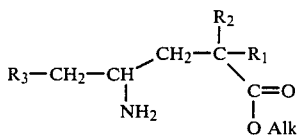
(II)

The preparation of (II), can be done by various methods.

When $R_3$ is different from thienyl, it is possible to operate according to the following reaction diagram:

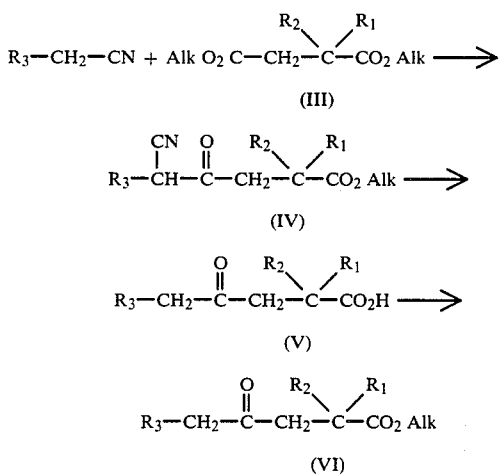

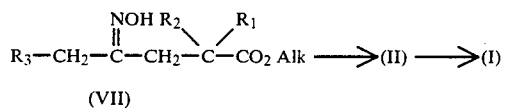

After having condensed the benzyl cyanide (optionally substituted) on the substituted succinic diester, in the presence of sodium ethylate, it is hydrolyzed in an acid medium to obtain the gamma keto-acid (V) which is then esterified in the usual way.

The gamma keto-ester (VI) is converted into the gamma amino ester (II), either by reducing amination by ammonium acetate in the presence of sodium cyanoborohydride, or by the formation of a gamma hydroximino ester which is subjected to catalytic hydrogenation.

To prepare the pyrrolidinones according to the invention which bear an alkyl substituent at the 3 position, it is possible to prepare (II) according to the following reaction diagram:

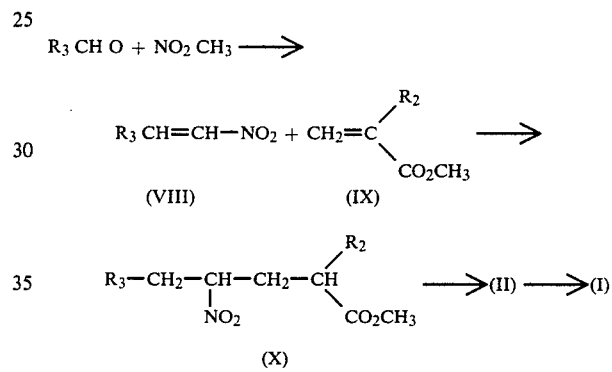

The condensation of a nitroalkane to an aldehyde to give a nitrostyrene is described in: J. Org. Chem., 1953, 18, p. 1 for benzaldehydes and in: J. Org. Chem., 1949, 14, p. 409, for thiophenaldehydes.

The addition, on nitrostyrene (VIII) of a methacrylate (IX), is done at ambient temperature in the presence of sodium borohydride in a solvent, such as dimethylsulfoxide.

By catalytic hydrogenation of (X), under a pressure of some atmospheres, the gamma-amino-ester is obtained which is not cyclized.

PROCESS 2

To prepare the pyrrolidinones according to the invention which are mono-substituted by an alkyl group (see compound SR 42 226), or by a mono-substituted by a trimethylsilyl group (see compounds SR 42 134 and SR 42 225), or disubstituted at the 3-position by two alkyl groups or one alkyl group and one trimethylsilyl group (see compound SR 42 133), at the 3-position, it is possible to use Process 2:

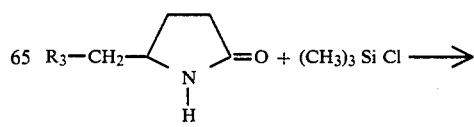

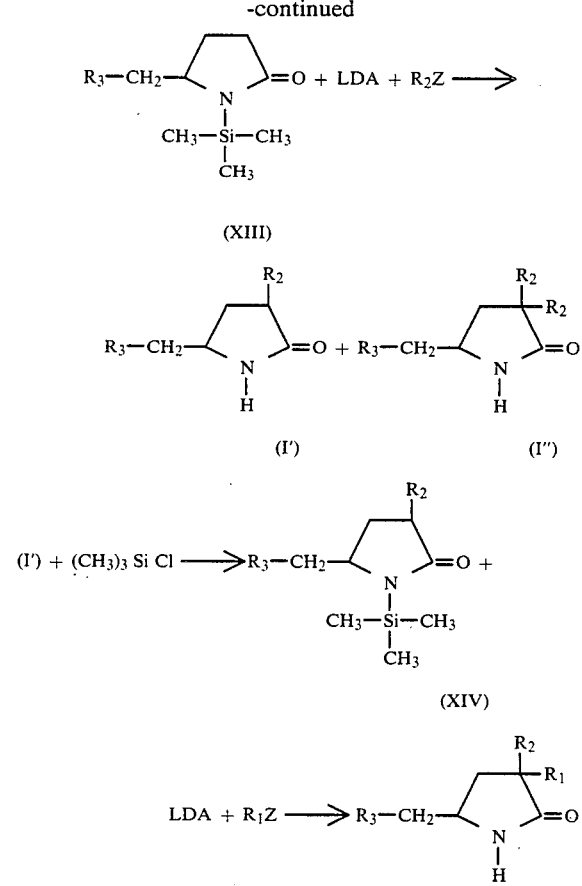

Substitution of the pyrrolidinone by $R_1$ and $R_2$ necessitates the protection of the NH by the trimethylsilyl group. By the action of lithium diisopropylamide (LDA), an anion is formed on which a halide $R_2$—Z (Z=Br or I if $R_2$=alkyl and Z=Cl if $R_2$=Si $(CH_3)_3$) is reacted. Besides the product mono-substituted at the 3 position by $R_2$, a product di-substituted at the 3 position by 2 $R_2$ radicals is obtained. From the mono-substituted product and a halide $R_1$—Z, the same reaction sequence leads to the product di-substituted by the radicals $R_1$ and $R_2$.

EXAMPLE 1

3-ethyl-5-[(2-fluoro-phenyl)-methyl]-3-methyl 2-pyrrolidinone: SR 42001

(a) Ethyl ester of 4-keto-2-ethyl-5-(2-fluoro-phenyl)2-methyl-pentanoic acid 18.5 g of sodium were dissolved in 250 ml of absolute ethyl alcohol, then 110 g of the dimethyl diester of 2-ethyl-2-methyl-succinic acid and 72 g of benzyl 2-fluoro cyanide were added. It was taken to reflux for 6 hours under stirring and then the stirring maintained overnight at room temperature.

After evaporation of the solvent, it was taken up again with 500 ml of water then extracted twice with 500 ml of ether. The aqueous phase was acidified to pH 4 with acetic acid, then it was extracted with chloroform, dried over sodium sulfate and the solvent evaporated under vacuum. To the residue 235 ml of water, 775 ml of acetic and 260 ml of concentrated hydrochloric acid were added, and then it was heated under reflux for 11 hours under nitrogen; the solution was then evaporated under vacuum, taken up again with dichloromethane, and washed with water; the organic phases were dried over sodium sulfate and concentrated under vacuum.

The residue was taken up again with 300 ml of absolute ethanol, 6 ml of concentrated sulfuric acid were added and then it was heated under reflux for 24 hours. After evaporation of the ethanol, it was taken up again with dichloromethane, washed with water, with a solution of saturated sodium bicarbonate, then by a saturated solution of sodium chloride and it was dried over sodium sulfate.

63 g of ethyl ester of 4-keto-2-ethyl-5-(2-fluoro-phenyl)-2-methyl-pentanoic acid was obtained.

(b) Ethyl ester of 2-ethyl-5-(2-fluoro-phenyl)-2-methyl 4-hydroxyimino-pentanoic acid 63 g of the gamma keto ester prepared above were dissolved in 360 ml of 96% (by volume) ethyl alcohol and 25 ml of water. 19 g of hydroxylamine hydrochloride and 35 g of hydrated sodium acetate were added. It was heated to reflux for 11 hours. After evaporation of the solvent, it was taken up again by dichloromethane, washed with water, with a saturated solution of sodium chloride then washed over sodium sulfate. The solvent was evaporated under vacuum and then the residue was chromatographed on 600 g of silica by an ethyl acetate-pentane (25/75 by volume) mixture.

20 g of the ethyl ester of 2-ethyl-5-(2-fluoro phenyl)-2-methyl-4-hydroxyimino pentanoic acid were obtained.

(c) SR 42001

20 g of the above oxime were placed in an autoclave, 100 ml of 90% acetic acid and 10 g of 5% platinum on carbon were added.

The hydrogenation was carried under 20 atmospheres, at ordinary temperature for 10 hours. After filtration on Hyflocell, the solvent was evaporated; the residue was taken up again with water, concentrated soda was added to pH 11 and without cooling. After 15 minutes it was extracted with dichloromethane, washed with water, then with a saturated solution of sodium chloride, it was dried over sodium sulfate then evaporated under vacuum. The residue was chromatographed on 250 g of silica, the eluent being a mixture of dichloromethane-ethyl acetate (60–40 by volume).

The product obtained was distilled, b.p=175°–180° C., under 0.01 mm Hg; 1.5 g of pyrrolidinone was obtained: SR 42001.

EXAMPLE 2

5[(4-fluoro-phenyl)-methyl]-3-methyl-2-pyrrolidinone: SR 41882

(a) Ethyl ester of 4-keto-5-(4-fluoro-phenyl-2-methyl pentanoic acid

The operation is carried out as in Example 1 and with the same amounts by reacting benzyl p-fluorocyanide with the methyl diester of 2-methyl-succinic acid.

The gamma keto ester obtained is distilled under vacuum; b.p.=120°–130° C. under 0.05 mm Hg. 42 g of product are recovered.

(b) SR 41882

42 g of the previously obtained product were dissolved in 800 ml of methanol, 135 g of ammonium acetate and then 7.8 g of sodium cyanoborohydride were added. After 16 hours of stirring, ¾ of the solution was evaporated under vacuum and then it was taken up again with 400 ml of water, 200 ml of acetic acid were added and it was then stirred for 1 hour before neutralizing with sodium bicarbonate. The pH was then brought to 11 with 30% soda, and the temperature rose to 50° C.

After 15 minutes stirring, it was extracted with dichloromethane, washed, dried over sodium sulfate and evaporated under vacuum then dried again for 1 hour at 90° C. under vacuum. The 30 g obtained were chromatographed on 700 g of silica using pure ethyl acetate as eluent.

After making into a paste with isopropyl ether, 13 g of SR 41882 were obtained; m.p. = 102° C.

EXAMPLE 3

3,3-dimethyl-5-[(4-fluoro-phenyl)-methyl]2-pyrrolidinone: SR 41293

This product was prepared by following the same process as for Example 2. After recrystallization in cyclohexane, m.p. = 114° C.

EXAMPLE 4

3-methyl-5-(2-thienyl-methyl)-2-pyrrolidinone, trans isomer (SR 42008); cis isomer (SR 42009)

(a) Methyl ester of 2-methyl-4-nitro-5-thienyl-pentanoic acid

To a solution of 23 g of 2-nitrovinyl-thiophene in 200 ml of dimethylsulfoxide, were added 21 g of methacrylate. Maintaining, with stirring, the temperature between 25° C. and 30° C., there were added, in portions, 2.82 g of powdered sodium borohydride.

After 14 hours stirring, 15 ml of water and 30 ml of acetic acid were added; it was poured into 1 liter of ice water and then stirred 30 minutes; it was extracted 5 times with 300 ml of ether and then washed 3 times with 400 ml of water, once with 400 ml of a saturated solution of sodium chloride, it was dried over sodium sulfate, and then the ether was evaporated off under vacuum. The residue was chromatographed on 800 g of silica, using as eluent a pentane-ethyl acetate (80/20 by volume) mixture.

The 2 diastereoisomers of the nitroester were obtained.

(b) SR 42008

4.5 g of the least polar nitroester were hydrogenated in 500 ml of 95% ethanol with T₁ Raney Nickel (1 coffee spoon) under 10 atmospheres for 24 hours.

It was filtered on Hyflocell, the solvent evaporated and then recrystallized in cyclohexane. 1.5 g of the trans isomer of the expected product was obtained: SR 42008; m.p. = 97° C.

(c) SR 42009

4.2 g of the most polar nitroester were hydrogenated under the same conditions to obtain 1.6 g of the cis isomer; SR 42009; m.p. = 117° C., after recrystallization in cyclohexane. Identification of the cis isomer was done by nuclear magnetic resonance by the nuclear Overhauser effect.

EXAMPLE 5

3-butyl-5-[(3-methoxy-phenyl)]-2-pyrrolidinone: SR 42223 and
3,3-dibutyl-5-[(3-methoxy-phenyl)]-2-pyrrolidinone: SR 42224

(a) 5-[(3-methoxy-phenyl)]-1-trimethylsilyl-2-pyrrolidinone

A solution of 5 g of 5-[(3-methoxy-phenyl)-methyl]2-pyrrolidinone in 60 ml of benzene was prepared to which was added 2.5 g of triethylamine and then, drop by drop, 3 g of trimethylsilyl chloride. It was heated to reflux for two and a half hours then cooled, filtered and the benzene evaporated under vacuum. 2.8 g of the expected product distilling at 170°-180° C. under 0.1 mm of Hg was obtained.

(b) SR 42223 and SR 42224

1.6 g of diisopropolyamine in 50 ml of dry tetrahydrofurane, were dissolved at −40° C., 8.53 ml of butyl-lithium added (1.6M in hexane) and stirring was maintained at this temperature under nitrogen for 20 minutes.

It was cooled to −70° C. and with stirring 3.2 g of the trimethylsilylpyrrolidone obtained at (a) in 20 ml of tetrahydrofurane was added, and after 30 minutes 1.8 g of bromobutane; 30 minutes later, it was allowed to come to room temperature and then placed under nitrogen overnight. Then a solution of ammonium chloride was added and after 30 minutes stirring, it was extracted with chloroform, washed, dried and evaporated.

The product was chromatographed on 180 g of silica, using as an eluant a mixture of ethyl acetate-dichloromethane (20–80 by volume). The disubstituted product (SR 42224) was eluted first and 0.35 g of it was obtained, then 1 g of the monosubstituted product (SR 42223), (mixture of cis and trans isomers). These products were in oily form, and they were identified by their nuclear magnetic resonance spectrum. The spectrum was recorded in deuterated chloroform at 60 MHz, using hexamethyldisiloxane as a reference.

The following abbreviations will be used:
S: singlet
Se: wide singlet
D: doublet
T: triplet
M: multiplet
J: coupling constant

SR 42223

1H at 7.30 ppm (T of D, J1=8 Hz, J2=2 Hz, H5')
3H at 6.80 ppm (M, H3', H4', H5')
1H at 5.95 ppm (Se, CONH)
1H at 3.80 ppm (M, H5)
3H at 3.80 ppm (S, O CH₃)

2H at 2.70 ppm (M, CH$_2$—aromatic)
9H between 2 and 1.5 ppm (M, H3, H4, (CH$_2$)$_3$)
3H at 0.82 ppm (T distorted, CH$_3$)

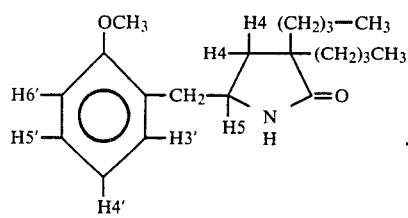

SR 42224

1H at 7.23 ppm (T of D, J$_1$=8 Hz, J$_2$=2 Hz, H5')
3H at 6.80 ppm (M, H3', H4', H6')
1H at 5.80 ppm (Se, CO NH)
3H at 3.73 ppm (S, OCH$_3$)
1H at 3.70 ppm (M, H5)
2H at 2.70 ppm (M, CH$_2$—aromatic)
14H between 1 and 2.2 ppm (M, H4, (CH$_2$)$_3$—CH$_3$)
6H at 0.82 ppm (T distorted, CH$_3$)

Other compounds according to the invention have also been prepared using one of the above-described processes. The values of the substituents R$_1$, R$_2$, R$_3$ are given in Table 1 below, as well as the boiling point (m.p.) or the solvent of recrystallization and the melting point (m.p.) of the products. The synthesis of each compound has been done by the technique described in the example mentioned between parentheses.

TABLE 1

| SR No. (Example) | R$_1$ | R$_2$ | R$_3$ | M.p. °C. (recrystallization solvent) or b.p. °C. (distillation pressure) |
|---|---|---|---|---|
| SR 41676 (1) | H | CH$_3$ | 2,4-dichlorophenyl | M.p. = 128 (CCl4) |
| SR 41677 (1) | CH$_3$ | CH$_3$ | 3,4-dimethoxyphenyl | M.p. = 80 (i Pr$_2$ O) |
| SR 41678 (1) | H | CH$_3$ | 2-chlorophenyl | B.p. = 180-185 (0.01 mm Hg) |
| SR 41680 (1) | CH$_3$ | CH$_3$ | 2-fluorophenyl | M.p. = 103 (i Pr$_2$ O) |
| SR 41773 (1) | H | phenyl | 3,4-dimethoxyphenyl | M.p. = 109 (i Pr$_2$ O) |
| SR 41873 (1) | CH$_3$ | CH$_3$ | 4-chlorophenyl | M.p. = 135 (i Pr$_2$ O) |
| SR 41880 (2) | CH$_3$ | CH$_3$ | 2-chlorophenyl | M.p. = 86 (i Pr$_2$ O) |
| SR 41881 (2) | H | CH$_3$ | 2-fluorophenyl | M.p. = 106 (i Pr$_2$ O) |
| SR 42002 (1) | CH$_3$ | C$_2$H$_5$ | 4-fluorophenyl | M.p. = 96 (i Pr$_2$ O) + cyclohexane |
| SR 42003 (1) | CH$_3$ | CH$_3$ | 4-methylphenyl | M.p. = 129 (i Pr$_2$ O) |
| SR 42004 (1) | H | CH$_3$ | 2-chloro, 6-fluorophenyl | M.p. = 70 (i Pr$_2$ O) |
| SR 42010 (4) | H | CH$_3$ | phenyl | M.p. = 92 (cyclohexane) |
| SR 42133 (5) | (CH$_2$)$_3$CH$_3$ | Si(CH$_3$)$_3$ | phenyl | M.p. = 88 (pentane) |
| SR 42134 (5) | H | Si(CH$_3$)$_3$ | phenyl | M.p. = 134 (i Pr$_2$ O) |
| SR 42225 (5) | H | Si(CH$_3$)$_3$ | 4-fluorophenyl | M.p. = 138 (i Pr$_2$ O) |
| SR 42226 (5) | H | (CH$_2$)$_2$CH$_3$ | 4-fluorophenyl | M.p. = 45 (i Pr$_2$ O) |
| SR 42353 (1) | CH$_3$ | CH$_3$ | phenyl | M.p. = 118 (i Pr$_2$ O) |
| SR 42354 (1) | H | CH$_3$ | 4-chlorophenyl | M.p. = 114 (i Pr$_2$ O) |
| SR 42401 (1) | H | CH$_3$ | 3-trifluoromethyl phenyl | M.p. = 110 (i Pr$_2$ O) |
| SR 42508 (1) | CH$_3$ | CH$_3$ | 2,4 dichlorophenyl | M.p. = 130 (i Pr$_2$ O) |
| SR 42717 (1) | H | CH$_3$ | 3-chlorophenyl | M.p. = 94 (i Pr$_2$ O) |
| SR 42725 (1) | CH$_3$ | CH$_3$ | 3-trifluoromethyl phenyl | M.p. = 92 (i Pr$_2$ O) |
| SR 42726 (1) | H | CH(CH$_3$)$_2$ | 4-chlorophenyl | M.p. = 104 (i Pr$_2$ O) |

*i Pr$_2$ O signifies isopropyl ether

The activity of the products according to the invention on the central nervous system was measured by various pharmacological tests. For each of these tests, there was also measured the activity of the product mentioned in Yakugaku Zasshi, 1960, 86 (12), p. 1213-1216: 5-phenylmethyl 2-pyrrolidinone that will be called compound A.

EFFECT OF THE PRODUCTS ON SPONTANEOUS MOTILITY

The spontaneous motility of the animals was measured by means of the activity test developed by Boissier and Simon, Arch. Int. Pharmacocyn., 1965, 158, 212-221. The equipment is composed of actimetric cages, type Apelab (26×21.5×10 cm), traversed by two light rays which fall on a photoelectric cell. The batches were constituted by $CD_1$ Charles Rivers female mice, of weight comprised between 20 and 24 g. The animals were placed individually in cages 45 minutes after oral administration of the products at the dose of 100 mg/kg. Each traversal by a light beam was counted by an individual counter. The scores corresponding to the movements of the animals were recorded for 10 minutes, and compared with the scores taken on batches of control animals, treated only with the vehicle (5% gum arabic).

TABLE 2

| Products at 100 mg/kg p.os. | Locomotor activity score percent/controls |
| --- | --- |
| SR 41676 | −34%* |
| SR 41678 | +45%* |
| SR 41680 | +99%** |
| SR 41881 | +41%** |
| SR 42008 | −52%** |
| SR 42009 | −23%* |
| Compound A | +1.2% |

*P < or = 0.05
**P < or = 0.01

After administration at the oral dose of 100 mg/kg certain products of the invention cause stimulating effects of the motor activity of the mouse (SR 41678; SR 41680; SR 41881) whereas others show a sedative activity characterized by a considerable reduction in the motility of the animals (SR 41676; SR 42008; SR 42009). The compound A does not act on the spontaneous motility.

POTENTIATION OF NARCOSIS WITH PENTOBARBITAL

For the purpose of evaluating the hypnogenic power of the products, their capacity to potentiate the effects of a subnarcotic dose of pentabarbital in the mouse was studied. The batches were constituted by 10 $CD_1$ Charles Rivers mice, of weight comprised between 20 and 24 g.

The pentobarbital (20 mg/kg, i.p.) was administered 60 minutes after administration of the products. The drowsiness criterion taken was the loss of the righting reflex. The animals which did not show this reflex were counted.

TABLE 3

| Products | Potentiation of Pentobarbital percent of animals in narcosis, products at 100 mg/kg p.os. |
| --- | --- |
| SR 41293 | 80% $ED_{50}$ = 56 (47–85)**1 |
| SR 41676 | 100% $ED_{50}$ = 48 (35–66)**1 |
| SR 41677 | 30% |
| SR 41678 | 30% |
| SR 41873 | 10% |
| SR 41880 | 40% |
| SR 41881 | 30% |
| SR 41882 | 20% |
| SR 42001 | 20% |
| SR 42002 | 50% |
| SR 42004 | 30% |
| Compound A | 0% |

**1: The $ED_{50}$ was calculated by the probit method, and the confidence limits, between parentheses, was established for the probability level P < or = 0.05.

The products according to the invention are suitable for potentiating narcosis with pentobarbital; this property is indicative of a hypnogenic effect. The compound A was devoid of hyponogenic effect.

EVALUATION OF THE ANTICONVULSANT ACTIVITY OF THE PRODUCTS

The anticonvulsant effect of the products in the mouse was evaluated on a model of convulsions caused by electric shock, and on 2 models of convulsions induced by chemical agents: bicuculline and 3-mercaptopropionic acid.

a—Antagonism of the convulsions induced by electric shock

The test was slightly modified from that of Swinyard et al., J. Pharm. Exp. Ther., 1952, 106, 319–330 and Asami et al. Arzneim. Forsch., 1974, 24 (1), 1563–1568. The equipment was composed of a Racia shock generator provided with two occular electrodes delivering a current of 60 volts for 0.3 seconds. The batches were constituted by 10 $CD_1$ Charles Rivers mice of weight comprised between 20 and 24 g. The products were administered orally, 60 minutes before the electroshock. The animals not exhibiting tonic extension of the rear limbs were considered as protected from the convulsive crisis.

TABLE 4

| Products | Median effective dose ($ED_{50}$) of electric shock antagonism (mg/kg p.os.) |
| --- | --- |
| SR 41293 | 99 (91–108)**1 |
| SR 41678 | 44 (36–54)**1 |
| SR 41680 | 51 (41–63)**1 |
| SR 41873 | 62 (48–80)**1 |
| SR 41881 | 92 (67–128)**1 |
| SR 42002 | 49 (30–79)**1 |
| SR 42004 | 34 (31–38)**1 |
| SR 42010 | 105 (69–160)**1 |
| SR 42354 | 34 (18–63)**1 |
| SR 42401 | 39 (22–61)**1 |
| SR 42508 | 50 (42–59)**1 |
| SR 42717 | 41 (31–55)**1 |
| SR 42725 | 34 (26–45)**1 |
| SR 42726 | 72 (58–91)**1 |
| Compound A | $ED_{50}$ undetermined Inhibition 40% at 200 mg/kg |

**1: The $ED_{50}$ was calculated by the probit method, and the confidence limits between parentheses was established for the probability level p < or = 0.05.

b—Antagonism of convulsions and of mortality caused by bicucullin

The batches were constituted by 10 CD Charles Rivers mice of weights comprised between 20 and 22 g. The products were administered orally, 60 minutes before the bicucullin (0.8 mg/kg, i.v.). The appearance of tonic convulsions as well as the mortality were noted for the 60 minutes which followed the injection of bicucullin.

TABLE 5

| | Median effective dose ($ED_{50}$) of the antagonism to the effects of bicucullin (mg/kg p.o.) | |
| --- | --- | --- |
| Products | Tonic convulsions | Mortality |
| SR 41293 | 90 (33–240)1 | 41 (30–55)1 |
| SR 41678 | 76 (52–111)1 | 76 (37–155)1 |
| SR 41873 | 112 (88–142)1 | 85 (67–109)1 |
| SR 42001 | 83 (36–180)1 | 62 (53–72)1 |
| SR 42002 | little different from 100 | little different from 100 |
| SR 42004 | little different from 100 | higher than 100 |
| SR 42354 | 63 (34–118)1 | 66 (31–142)1 |
| SR 42401 | 62 (44–87)1 | 72 (40–129)1 |
| SR 42508 | little different from 100 | 73 (33–159)**1 |
| SR 42717 | little different from 100 | 59 (32–109)**1 |
| SR 42725 | little different from 100 | 66 (40–110)**1 |

TABLE 5-continued

| Products | Median effective dose (ED$_{50}$) of the antagonism to the effects of bicucullin (mg/kg p.o.) | |
|---|---|---|
| | Tonic convulsions | Mortality |
| Compound A | inactive at 200 | ED$_{50}$ undetermined 30% Antagonism at 200 |

**1: The ED$_{50}$ was calculated by the probit method, and the confidence limit between the parentheses was established for the probability level p < 0.05.

c—Antagonism to the convulsions caused by 3-mercaptopropionic acid

The batches were constituted by 10 CD Charles Rivers mice of weights comprised between 20 and 22 g. The products were administered orally 60 minutes before the 3-mercaptopropionic acid (60 mg/kg s.c.). The appearance of tonic convulsions was noted for the 60 minutes which followed the administration of 3-mercaptopropionic acid.

TABLE 6

| Products | Median effective dose (ED$_{50}$) of antagonism to convulsions caused by 3-mercaptopropionic acid (mg/kg p.o.) |
|---|---|
| SR 41293 | 20 (17–23)**1 |
| SR 41676 | 23 (18–29)**1 |
| SR 41678 | 53 (38–75)**1 |
| SR 41680 | 54 (36–80)**1 |
| SR 41873 | 48 (37–64)**1 |
| SR 41881 | 46 (35–62)**1 |
| SR 41882 | 41 (30–56)**1 |
| SR 42002 | 49 (32–74)**1 |
| SR 42004 | 27 (18–39)**1 |
| SR 42010 | 44 (22–90)**1 |
| SR 42354 | 40 (25–36)**1 |
| Compound A | Higher than 100 |

**1: The ED$_{50}$ was calculated by the probit method, and the confidence limits between parentheses were established for the probability level p < or = 0.05.

After oral administration in the mouse, the products according to the invention show anticonvulsant properties, both with respect to electric shock and bicucullin and 3-mercaptopropionic acid. On the contrary, compound A does not show anticonvulsant properties.

The toxicity of the products according to the invention was studied: the products were administered orally, to batches of 5 CD Charles Rivers female mice, of weights comprised between 20 and 24 g. The toxicity was noted during the 72 hours which followed the administration of the products.

TABLE 7

DETERMINATION OF THE LETHAL DOSE IN THE MOUSE AFTER ACUTE ADMINISTRATION OF THE PRODUCTS

| Products | Percent toxicity | | |
|---|---|---|---|
| | 250 mg/kg p.o. | 500 mg/kg p.o. | 1000 mg/kg p.o. |
| SR 41293 | 0 | 0 | 80 |
| SR 41676 | 0 | 0 | 0 |
| SR 41677 | 0 | 0 | n.d. |
| SR 41678 | 0 | 0 | 60 |
| SR 41680 | 0 | 0 | n.d. |
| SR 41773 | 0 | 0 | n.d. |
| SR 41873 | 0 | 0 | n.d. |
| SR 41880 | 0 | 0 | 20 |
| SR 41881 | 0 | 0 | 100 |
| SR 41882 | 0 | 0 | 100 |
| SR 42001 | 0 | 0 | 20 |
| SR 42002 | 0 | 0 | 100 |
| SR 42003 | 0 | 0 | 0 |
| SR 42004 | 0 | 0 | 0 |
| SR 42008 | 0 | 0 | 0 |
| SR 42009 | 0 | 0 | 40 |
| SR 42010 | 0 | n.d. | n.d. |
| SR 42133 | 0 | 0 | 0 |
| SR 42134 | 0 | 0 | 0 |
| SR 42354 | 0 | 0 | n.d. |
| SR 42401 | 0 | 0 | n.d. |
| SR 42508 | 0 | 0 | 0 |
| SR 42717 | 0 | 0 | 100 |
| SR 42725 | 0 | 0 | 0 |
| SR 42726 | 0 | 0 | 20 |
| Compound A | 0 | 0 | 60 | n.d. signifies undetermined

The results expressed as a percentage of animals which die in the 72 hours following the oral administration of the products, are noted in the preceding table.

The lethal doses were considerably higher than their active doses in the pharmacological tests described in the preceding paragraphs.

The tests thus carried out show that the products according to the invention have interesting pharmacological properties and low toxicity. Consequently, they can be used in human therapeutics particularly for treatment of psychic, neurological or neuromuscular disorders.

In particular, the products according to the invention may be used for treatment of mood or behavior disorders, nervousness, irritability as well as for treatment of anxiety states, insomnia and epilepsy.

These products may be administered orally or by injection. The pharmaceutical compositions can be solid or liquid and presented, for example, in the form of tablets, capsules, granulates, suppositories or injectable preparations.

The posology can vary, within wide proportions, in particular, according to the type and seriousness of the disorder to be treated and according to the mode of administration. Mostly, in the adult orally, it is comprised between 1 mg and 500 mg per day, optionally distributed into several doses.

By way of example, the following galenic preparation may be indicated:

| CAPSULES: | |
|---|---|
| SR 42354 | 50 mg |
| Aerosil | 0.5 mg |
| Magnesium Stearate | 1.5 mg |
| Starch STA RX 1500 | 48 mg |
| | 100 mg |

We claim:

1. Pyrrolidinones of the formula:

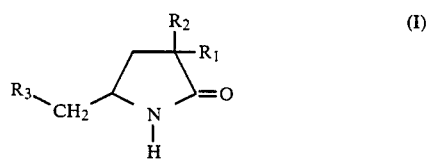

(I)

in which:

R$_1$ represents a hydrogen atom or a straight or branched alkyl group having 1 to 4 carbon atoms;

$R_2$ represents a straight or branched alkyl group having 1 to 4 carbon atoms, a phenyl group or a trimethylsilyl group;

$R_3$ represents a 2-thienyl group, an unsubstituted phenyl group, or a phenyl group substituted by one or two halogen atoms, methyl groups, methoxy groups, or trifluoromethyl groups.

2. A compound according to claim 1, wherein $R_3$ represents a chlorophenyl or a trifluoromethylphenyl group.

3. A compound according to claim 1, wherein $R_1$ represents a hydrogen atom, $R_2$ represents a methyl group, and $R_3$ represents a 4-chloro-phenyl group.

4. A compound according to claim 1, wherein $R_1$ represents a hydrogen atom, $R_2$ represents a methyl group, and $R_3$ represents a 3-trifluoromethyl-phenyl group.

5. A compound according to claim 1, wherein $R_1$ represents a hydrogen atom, $R_2$ represents a methyl group, and $R_3$ represents a 2-chloro-phenyl or a 3-chloro-phenyl group.

6. A compound according to claim 1, wherein $R_1$ and $R_2$ each represent a methyl group and $R_3$ represents a trifluoromethyl-phenyl group.

7. A pharmaceutical composition for treatment of psychic, neurological or neuromuscular disorders, containing as active ingredient an effective amount for treating said disorders of at least one compound according to claim 1, in association with a pharmaceutically acceptable vehicle.

8. A pharmaceutical composition according to claim 7 wherein the active ingredient is present in an amount of from 1–500 mg., and the composition is packaged for oral or injectable administration.

* * * * *